(12) United States Patent
Kumar et al.

(10) Patent No.: US 7,429,478 B2
(45) Date of Patent: Sep. 30, 2008

(54) MICROBIAL CONSORTIUM USEFUL AS SEEDING MATERIAL FOR BOD ANALYSIS OF PULP AND PAPER INDUSTRIAL WASTEWATER

(75) Inventors: Rita Kumar, Delhi (IN); Shikha Rastogi, Delhi (IN); Anil Kumar, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 253 days.

(21) Appl. No.: 11/024,028

(22) Filed: Dec. 28, 2004

(65) Prior Publication Data

US 2006/0141553 A1    Jun. 29, 2006

(51) Int. Cl.
*C12N 1/20* (2006.01)
(52) U.S. Cl. .................................. 435/252.4; 424/93.3
(58) Field of Classification Search .............. None
See application file for complete search history.

(56) References Cited

U.S. PATENT DOCUMENTS

| 5,952,188 A | 9/1999 | Kumar et al. |
| 6,511,822 B1 | 1/2003 | Kumar et al. |

OTHER PUBLICATIONS

Ringe, Einar, Canadian Journal of Microbiology (1993), 39(12), 1169-73.*

* cited by examiner

*Primary Examiner*—Irene Marx
(74) *Attorney, Agent, or Firm*—Ladas and Parry LLP

(57) ABSTRACT

The present invention provides a seeding material for accurate and reproducible monitoring of BOD load of pulp and paper wastewater, wherein the bacteria are isolated from various locations in India and comprise *Micrococcus* sp., *Staphylococcus* sp., *Kurthia zopfii, Alcaligenes faecalis,* and *Pseudomonas aeruginosa,* the microbial composition being capable of exerting an appropriate BOD for pulp and paper industrial wastewater due to the specificity of bacterial strains present therein towards the refractory organic compounds found in these effluents.

4 Claims, No Drawings

MICROBIAL CONSORTIUM USEFUL AS SEEDING MATERIAL FOR BOD ANALYSIS OF PULP AND PAPER INDUSTRIAL WASTEWATER

FIELD OF THE INVENTION

The present invention relates to a process for preparing a specifically designed seeding material for BOD analysis of pulp and paper wastewater. The seeding material is a uniformly formulated microbial consortium comprising of isolated, acclimatized and synergistic bacterial rains.

BACKGROUND AND PRIOR ART

Most water analysis methods quantify individual components. However, some, such as oxygen demand tests quantify an aggregate amount of constituents with a common characteristic. Broadly speaking, BOD and COD quantify amount of oxygen required to oxidize organic matter in water/wastewater to indicate amount of organic material present. BOD utilizes microorganisms to oxidize organic material, while COD uses inorganic chemical oxidant. BOD measurement is the most fundamental way of determining water pollution levels and of predicting possible effects of waste discharge. Organic matter that is present in water can be from plants, sugars, proteins or other substances that enter water film natural sources or pollution. This matter is broken down biochemically by organisms such as bacteria, which can multiply as long as organic matter is present as food and oxygen is available for respiration. If high population of bacteria continuously consume dissolved oxygen in water at an accelerated rate, atmospheric air will not be able to replenish it. This situation can create a lack of dissolved oxygen in water, threatening and destroying many forms of aquatic life. Oxygen depletion in receiving waters has been regarded as an important negative effect of water pollution. Depletion takes place due to microbes consuming organic matter in water via aerobic respiration. This type of respiration uses oxygen as an electron accepter and organic material being consumed provides the energy source. Since $O_2$ content is important for may biological and chemical processes, measurements of amount of $O_2$ actually dissolved in a water sample is of great importance. BOD test relates to amount of $O_2$ that would be required to stabilize waste after discharging to a receiving water body. BOD is a parameter of great concern. Failing to realize importance of BOD in wastewater/effluent treatment systems can lead to devastating effects on local aquatic ecology and quality of underlying groundwater.

Monitoring BOD removal a treatment plant is necessary to verify proper operation. BOD test is typically performed in municipal or industrial wastewater plant. The results of BOD analysis are used to calculate the degree of pollution and to determine the effectiveness of water treatment by waste water and sewage plant. Different organic compounds show different oxygen demand (mg/l), thus the BOD test only gives an approximate idea of the weight of utilizable organic matter. BOD test is carried out using standard methods as prescribed in APHA (*Standard Method for the Examination of Water and Wastewater*, $20^{th}$ edn. 5-1-5-6. Baltimore). Test substances and standard substances are dissolved in BOD dilution water. Standard substrate is made of 0.15 mg/l glucose and 0.15 mg/l glutamic acid, which has a calculated BOD of 220 $mgL^{-1}$. It is expressed in terms of Dissolved Oxygen (DO), which microorganisms, mainly bacteria will consume while degrading organic material in a sample of water under standardized conditions of pH nutrient and microorganisms. The amount of oxygen that dissolves in the water depends on many factors: whether there is adequate time and adequate mixing to fully saturate the water, the water temperature, the air pressure, the salt content of the water, and whether there are substances in the water which consume the $O_2$ Microorganisms either are present in the water sample or are introduced by taking a small quantity of a suitable microbial source such as settled sewage. The inoculants is called BOD 'seed' and the process, 'seeding'. Since BOD analysis relies on a biological process, there is a greater variance in results then would normally be expected in a strictly chemical assay. The Standard methods for the Examination of Water and Wastewater indicated an acceptable range of ±15% at the 200 mg/l level for the reference GGA (Glucose-Glutamic Acid) solution; using the results from a series of Interlaboratory studies.

For all sources of seed, the possibility exists that some wastes will cause poisoning of the microorganisms. Some wastes will have develop3ed microorganisms adapted to the toxic conditions and hence give expected BOD results. But, in other wastes the microorganisms will adapt over the period of the BOD test. Because of the lag time involved in adaptation, a lower BOD is obtained than might be excepted. If the toxicity is sufficiently acute, a zero or close to zero result is obtained. Further, the ratio of various species of bacteria normally added can change in a 5-day period. BOD is the result of a summation of the oxygen demand of these microorganisms, whose contribution to the oxygen demand will change with time because of the changing population and changing feedstock.

Among the major industries in India, Pulp and Paper is one of those that contribute heavily to water pollution. Pollutants that generally arise from the industry include wood sugars, cellulose, fiber, lignin and other spent chemicals, which impart high BOD, COD, color, etc. to the effluent. Thus, there arises a need to develop specific seeding (comprising of selected, acclimatized and autochthonous bacterial strains) for analyzing the BOD load of these industrial wastewaters.

In addition, some of these compounds are refractory to biodegradation because of high molecular weight coupled with lesser bioavailability. The BOD analysis of such types of wastewaters poses acute problems because of many reasons, which include the heterogeneity of the samples from time to time, non-specific microorganisms present in general seeding material and lower biodegradation rate of the organic constituents present therein.

The aforesaid problems can be overcome by formulating a uniform microbial composition comprising selected isolated bacterial strains, acclimatized to pulp and paper wastewater. Further, these bacterial isolates must be specific for biodegradation of organic compounds present in these kinds of wastewater. General seeding materials viz., sewage, Polyseed, Bioseed and BODSEED™, when used for BOD analysis of above said wastewater does not work efficiently because of non-specificity of bacterial strains present therein. This leads to erroneous results, which differ from time to time. On the other hand, if specifically designed formulated microbial consortium comprising selected bacterial strains are used as seed for BOD analysis of above said effluents, it may yield reproducible and reliable results.

Thus, for solving the aforementioned problems, the applicants have realized that there exists a need to provide a process for the preparation of a microbial consortium, specifically formulated for use as seeding material for the BOD analysis of Pulp and paper wastewater.

OBJECT OF THE INVENTION

The main object of the invention is to provide a specific seeding mated for the BOD estimation of pulp and paper effluents.

Another object of the invention is to provide a microbial consortium exerting a synergistic effect for the assimilation of pulp and paper wastewater.

Another object of the invention is to provide a process for preparing a microbial consortium specifically formulated for use as seeding material in BOD analysis of pulp and paper wastewater.

SUMMARY OF THE INVENTION

The present invention relates to a process for development of a microbial composition consortium selected acclimatize bacterial Us, isolated from source habitat. The bacterial strains constituting THE microbial consortium are synergistic and exert an exact and reproducible oxygen demand for pulp and paper wastewater. The present invention provides a formulated microbial consortium and a process for the preparation of the said consortium, useful for reliable and reproducible BOD estimation of pulp and paper industrial wastewater.

Accordingly the present invention provides a synergistic microbial consortium for use as a seeding material for estimation of accurate and reproducible biochemical oxygen demand of pulp and paper industrial waste water, the composition comprising five bacterial strains, *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605) deposited at International Depository at IMTECH, Sector 39A, Chandigarh, India.

In one embodiment of the invention, bacterial strains are taken in equal proportions.

In another embodiment of the invention, the bacteria are isolated from activated sludge and soil samples collected from the vicinity of a selected pulp and paper mill.

In another embodiment of the invention, the characteristics of *Micrococcus* sp (MTCC 6602) are as follows: Gram—positive, Shape—coccid, In another embodiment of the invention, the characteristics of *Staphylococcus* sp. (MTCC 6603) are as follows: Gram—positive, Shape—rods.

In another embodiment of the invention, the characteristics of *Kurthia zopfii* MTCC 6604) are as follows: Gram—Negative, Shape—rods.

In another embodiment of the invention, the characteristics of *Alcaligenes faecalis* (MTCC 6719) are as follows: Gram—Negative, Shape—rods, In another embodiment of the invention, the characteristics of *Pseudomonas aerations* (MTCC 6605) are as follows: Gram—Negative, Shape—rods.

The present invention also relates to a process for preparing a microbial consortium for use as a seeding material for estimation of accurate and reproducible biochemical oxygen demand of pulp and paper industrial waste water, the consortium comprising five bacterial strains, *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605) deposited at International Depository at IMTECH, Sector 39A, Chandigarh, India, the process comprising inoculating individual bacterial strains of bacteria separately in a nutrient broth, incubating the cultures, measuring cell colony growth at periodic intervals till required growth is attained, mixing individual cultures in desired proportions to form cell suspension, centrifuging cell suspension to obtain a cell pellet and washing the cell pellet, re-centrifuging the cell pellet to obtain a final cell pellet and suspending final cell pellet in phosphate buffer.

In yet another embodiment of the invention, cell colony growth is determined by measuring optical density of all cultures at 620 nm after stipulated time intervals till required growth where optical density is in the range of 1.0 to 1.2 at 650 nm is attained.

In another embodiment of the invention, cell cultures are incubated at a temperature in the range of 30-37° C. for approximately 12-18 hours and under gentle shaking.

In one embodiment of the invention, the nutrient broth contains per litre, 5.0 g of Peptic digest of a tissue; 5.0 g of Sodium chloride; 1.5 g of Beef extract; 1.5 g of Yeast extract and 0.1 ml Tween-80.

In another embodiment of the invention, the resultant cell suspension is centrifuged at an rpm in the range of 6000-8000 and for a period in the range of 15-25 minutes and at a temperature between 4-12° C.

In another embodiment of the invention, the cell pellet is washed by dissolving in 10-100 mM phosphate buffer having a pH in the range of 6.5-7.5 followed by vortexing for 35-45 seconds, followed by recentrifugation at in the range of 5000-8000 rpm for 15-25 minutes and at a temperature ranging between 4-10° C.

In another embodiment of the invention, the cell pellet washed once is given a second wash with 10-100 mM phosphate buffer having a pH in the range of 6.5-7.5.

In another embodiment of the invention, the cell pellet is suspended in 5.0-10.0 ml of 10-100 mM phosphate buffer having a pH in the range of 6.5-7.5.

In another embodiment of the invention, the cell pellet is washed twice by dissolving in minimum quantity of 50 mM phosphate buffer having a pH 6.8.

In another embodiment of the invention, the re-centrifugation of the washed cell pellet is carried out at a rpm of about 5000 rpm and for a period of about 20 minutes and at a temperature ranging between 4-10° C.

In a further embodiment of the invention, the recentrifuged cell pellet is suspended in desired volume of phosphate buffer and stored at a temperature of about 4° C., till use.

In one embodiment of the invention, bacterial strains are taken in equal proportions.

In another embodiment of the invention, the bacteria are isolated from activated sludge and soil samples collected from the vicinity of a selected pulp and paper mill.

In another embodiment of the invention, the characteristics of *Micrococcus* sp., (MTCC 6602) are as follows: Gram—positive, Shape—coccid.

In another embodiment of the invention, the characteristics of *Staphylococcus* sp. (MTCC 6603) are as follows: Gram—positive, Shape—rods.

In another embodiment of the invention, the characteristics of *Kurthia zopfii* (MTCC 6604) are as follows: Gram—Negative, Shape—rods.

In another embodiment of the invention, the characteristics of *Alcaligenes faecalis* (MTCC 6719) are as follows; Gram—Negative, Shape—rods.

In another embodiment of the invention, the characteristics of *Pseudomonas aerations* (MTCC 6605) are as follows: Gram—Negative, Shape—rods.

The present invention also provides a method for the estimation of biochemical oxygen demand of pulp and paper industrial wastewater using a consortium comprising five bacterial strains, *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605) deposited at International Depository at IMTECH, Sector 39A, Chandigarh, India, the process comprising treating pulp and paper industrial wastewater with the microbial consortium and analyzing the biochemical oxygen demand thereof.

In one embodiment of the invention, the bacterial strains are taken in equal proportions.

In another embodiment of the invention, the bacteria are isolated from activated sludge and soil samples collected from the vicinity of a selected pulp and paper mill.

In another embodiment of the invention, the characteristics of *Micrococcus* sp. (MTCC 6602) are as follows: Gram—positive, Shape—coccid.

In another embodiment of the invention, the characteristics of *Staphylococcus* sp. (MTCC 6603) are as follows: Gram—positive, Shape—rods.

In another embodiment of the invention, the characteristics of *Kurthia zopfii* (MTCC 6604) are as follows: Gram—Negative, shape—rods, In another embodiment of the invention, the characteristics of *Alcaligenes faecalis* (MTCC 6719) are as follows, Gram—Negative, Shape—rods.

In another embodiment of the invention, the characteristics of *Pseudomonas aerations* (MTCC 6605) are as follows: Gram—Negative, Shape—rods, The present invention also provides a method for eating biochemical oxygen demand of pulp and paper industrial wastewater using a consortium comprising five bacterial strains, *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605), the process comprising:

a) isolating a range of bacterial strains from soil near selected pulp and paper industries;

b) culturing the strains on a nutrient medium to obtain pure cultures;

c) inoculating isolated bacterial strains individually in nutrient medium and incubating them at ambient temperature under gentle shaking for a period of 12-18 hrs;

d) observing optical density of the cultures at 620-650 nm till desired growth is attained;

e) harvesting grown cells obtained in step (d) by centrifuging for 15-25 min at a temperature in the range of 4 to 10° C. to obtain a cell pellet;

f) washing cell pellet obtained in step (e) by dissolving in 10-100 mM phosphate buffer having pH in the range of 6.5-7.5 followed by recentrifugation;

g) repeating step (f) for giving a second washing to the obtained cell pellet;

h) dissolving pellet obtained from step (g) in desired volume of 10-100 mM phosphate buffer with pH in range of 6.5-7.5 to obtain a seed for BOD analysis of pulp and paper wastewater;

i) testing individual pure cultures of isolated bacterial strains obtained in step (h) for analyzing BOD of pulp and paper industrial wastewater;

j) verifying BOD values obtained in step (i) using a reference standard;

k) comparing the BOD values obtained in step (i) and (j) with values obtained using a synthetic seed;

l) select bacterial strains which have BOD values equal to or more than BOD values obtained using the synthetic seed as seeding material observed in step (k);

m) bacterial strains selected in step (l) in various combinations to obtain different microbial consortia;

n) obtaining cell pellet of each microbial consortium following the method of steps c to h;

o) testing seeds as obtained in step (n) for BOD analysis of pulp and paper wastewater, p) selecting the optimal seed from results as obtained in step (o).

In one embodiment of the invention, the cell slurry of individual isolated bacterial strains is tested as seed for BOD analysis of pulp and paper wastewater.

In another embodiment of the invention, the BOD values obtained using seeds are verified using Glucose-Glutamic acid (GGA) as a reference standard.

In one embodiment of the invention, the bacterial strains are taken in equal proportions.

In another embodiment of the invention, the bacteria are isolated from activated sludge and soil samples collected from the vicinity of a selected pulp and paper mill.

In another embodiment of the invention, the characteristics of *Micrococcus* sp. (MTCC 6602) are as follows: Gram—positive, Shape—coccid.

In another embodiment of the invention, the characteristics of *Staphylococcus* sp. (MTCC 6603) are as follows: Gram—positive, Shape—rods.

In another embodiment of the invention, the characteristics of *Kurthia zopfii* MTCC 6604) are as follows: Gram—Negative, Shape—rods.

In another embodiment of the invention, the characteristics of *Alcaligenes faecalis* (MTCC 6719) are as follows: Gram—Negative, Shape—rods.

In another embodiment of the invention, the characteristics of *Pseudomonas aerations* (MTCC 6605) are as follows: Gram—Negative, Shape—rods,

DETAILED DESCRIPTION OF THE INVENTION

The specific seeding material provided according to the present invention is a formulated microbial consortium, which contains bacteria consisting of:

| Sl. No. | Culture | Identification no. | Deposition No. |
|---|---|---|---|
| 1 | Micrococcus sp. | MTCC 6602 | 5198 |
| 2 | Staphylococcus sp | MTCC 6603 | 5199 |
| 3 | Kurthia zopfii | MTCC 6604 | 5200 |
| 4 | Alcaligenes faecalis | MTCC 6719 | 5201 |
| 5 | Pseudomonas aeruginosa | MTCC 6605 | 5202 | and which facilitate BOD analysis of pulp and paper wastewater, giving accurate and reproducible BOD values of these wastewaters, performed at any place. The above mentioned bacterial strains are deposited at the International Depository at IMTECH, Sector 39A, Chandigarh, India recognized by Budapest Treaty and will be available to public on request as per the normal official procedures. The main characteristic features of all bacterial isolates used for the present invention are given below:

*Micrococcus* sp. (MTCC 6602)

*Micrococcus* sp. (MTCC 6602) is aerobic in nature, is gram positive, motile, capable of growth at pH 8.00 and in NaCl (8.5%) and shows opium growth at 37° C. and is also capable of hydrolyzing urea and starch.

*Staphylococcus* sp. (MTCC 6603)

*Staphylococcus* sp. (MTCC 6603) is facultative aerobic in nature, is gram positive, non-motile, shows optimum growth at 42° C., is also capable of growth at a pH of up to 11.00 and is capable of utilizing calaboose and silicon.

Kurthia Zopfli (MTCC 6604)

*Kurthia zopfii* (MTCC 6604) is facultative aerobic in nature, is gram positive, motile, shows optimum growth at 30° C. and is capable of growth at high pH (11.00) and is capable of utilizing calaboose and raffinose.

*Alcaligenes faecalis* (MTCC 6719)

*Alcaligenes faecalis* (MTCC 6719) is aerobic in nature, is gram negative, motile, shows optimum growth at 37° C. and is positive for cytochrome oxidize and catalane test and is also capable of utilizing dextrose and galactose as carbon source.

*Pseudomonas aerations* (MTCC 6605)

*Pseudomonas aerations* (MTCC 6605) is aerobic in nature, is gram negative, motile, fluorescent, shows optimum growth at 40° C., is capable of utilizing arabinose, dextrose, fructose, galactose, manifold, mannose and xylems.

The formulated microbial consortium preferably contains the bacteria in uniform amounts. The microbial consortium of the invention is useful as seeding material for the BOD analysis of especially, pulp and paper wastewater. The bacterial cultures of the above seeding material are isolated from selected source habitats. The source habitats are soils near pulp and paper industry, which have accumulated industrial wastewater for several years.

The specifically formulated seeding material is prepared by inoculating individual bacterial strains of the above mentioned bacteria separately in nutrient broth containing (per litre), 5.0 g of Peptic digest of animal tissue; 5.0 g of Sodium chloride; 1.5 g of Beef extract; 1.5 g of Yeast extract and 0.1 ml Tween-80. Incubation of all cultures is done preferably at a temperature of 37° C. for approximately 12-18 hours, under gentle shaking. Optical density of all cultures is measured at 620 nm after stipulated time intervals. After attaining required growth (O.D.=1.0-1.2 at 650 nm) in terms of optical density, individual cultures are mixed in desired proportions to formulate different microbial consortia.

The resultant cell suspension is centrifuged at an appropriate rpm (6000-8000) for a period of 20 minutes at a temperature between 4-12° C. The obtained cell pellet is washed twice by dissolving in minimum quantity of 50 mM phosphate buffer, pH 6.8 and recentrifuged at an appropriate rpm, preferably at 5000 rpm for a period of approximately 20 min at a temperature ranging between 4-10° C. The final cell pellet thus obtained is suspended n desired volume of phosphate buffer and stored at a temperature, preferably 4° C., till used.

The formulated microbial consort prepared in the above manner can be used as seed inoculum for the BOD analysis of specifically pulp and paper wastewater, using Glucose-Glutamic acid (GGA) as a pence standard. For this, desired aliquots of the prepared cell suspension, was added as seeding material in the dilution water for BOD. In the invention, BOD analysis was performed as per the method described in the Standard Method for the Examination of Water and wastewater (APHA, 1998).

The invention provides a microbial consortium comprising of a synergistic mixture of at least the following isolated bacterial strains present in equal proportions useful for analyzing the biochemical oxygen demand of especially, pulp and paper wastewater. The invention also provides a process for preparing the microbial formulation, which comprises:

a) isolating a range of bacterial isolates from soils near selected pulp and paper industries;

b) culturing the isolated bacterial isolates on nutrient medium (Ingredients: peptic digest of animal tissue −5 g/l; Sodium Chloride −5 g/l ; Beef extract −1.5 g/l and Yeast extract −1.5 g/l) to obtain pure cultures;

c) inoculating the isolated bacterial isolates individually in nutrient medium (Ingredients: peptic digest of animal tissue −5 g/l; Sodium Chloride −5 g/l; Beef extract −1.5 g/l and Yeast extract −1.5 g/l) and incubating them at an ambient temperature under gene shaking for a period of 12-18 hrs;

d) observing the optical density of the grown cultures at 620 nm;

e) harvesting the cells obtained in step (d) by centrifuging for 15-25 min at a temperature preferably at 4° C.;

f) washing the cell pellet obtained in step (e) by dissolving in 10-100 mM phosphate buffer, pH 6.5-7.5 followed by recentrifugation;

g) repeating step (f) for giving a second washing to the obtained cell;

h) dissolving the pellet obtained from step (g) in desired volume of 10-100 mM phosphate buffer, pH 6.5-7.5 to obtain the desired seed for BOD analysis of Pulp aid paper wastewater;

i) testing the individual pure cultures of the isolated bacterial strains as obtained in step (h) for analyzing the BOD of Pulp and paper industrial wastewater;

j) BOD estimation of pulp and paper industrial waster using specific bacterial isolates and bacteria present in BODEED
k) comparing the BOD values obtained in step (i) and (j) with those obtained using the synthetic seed viz., BOD-SEED™;
l) selecting the bacterial strains which have BOD values equal to more than the BOD values obtained using BOD-SEED as seeding material, as observed in step (k);
m) mixing the bacterial strains selected in step (l) in various combinations to obtain different microbial consortia;
n) obtaining the cell pellet of each microbial consortium in the manner as described in step c, d, e, f, g and h;
o) testing different microbial consortia as seeds as obtained in step (n) for the BOD analysis of pulp and paper industrial wastewater;
p) select the best seed from the results as obtained in step (o).

The microbial consortium comprises of a synergistic mixture of *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605). The bacterial strains are isolated from source habitats, which are soils near selected pulp and paper industry. The isolated bacterial strains were cultured on nutrient medium to obtain pure cultures. The individual bacterial strains isolated as stated above, were inoculated separately in nutrient medium followed by incubation at 30-37° C. for 12-18 hrs at 75-150 rpm. Optical density of the grown bacterial strains is observed at 620-650 nm. The obtained cell suspension having desired optical density is centrifuged at an appropriate rpm, preferably at 5000-8000 rpm for a period of approximately 15-25 min at a temperature ranging between 4-10° C. to harvest the cells. The harvested cell pellet is washed twice by dissolving in appropriate quantity of 10-100 mM phosphate buffer, pH 6.5-7.5, followed by centrifugation at an appropriate rpm in the range of 5000-8000 rpm for 15-25 min at a temperature preferably at 4° C. The washed cell pellet is dissolved in appropriate volume of 10-100 mM phosphate buffer, pH 6.5-7.5 to obtain the seed(s) for BOD analysis. The seeds thus obtained are tested for their efficiency towards BOD analysis of pulp and paper wastewater. BOD values of pulp and paper wastewater obtained using the seeds are compared with those using a synthetic seed viz., BODSEED™. The bacterial strains comprising the seeds, which exert BOD values equal to or more than BOD values observed using BODSEED™ are selected. The bacterial strains selected are then mixed in various combinations to obtain different microbial consortia. The cell pellet of each microbial consortium is obtained by the method described above. The microbial seeds thus obtained are tested for the BOD analysis of pulp and paper wastewater. The formulated microbial consortium exhibiting highest BOD for pulp and paper wastewater is selected for use as specific seeding material in BOD analysis of pulp and paper wastewater.

The invention is described with references to the following examples and should not be construed to limit the scope of the invention.

EXAMPLE 1

Isolation of the Bacterial Strains from the Source Habitat

Soil samples in vicinity of a selected pulp and paper Mill (Century Pulp & Paper Mill, LalKuan, Uttaranchal) were selected for isolation of bacterial strains. Different media were chosen for isolation, and are listed in Table 1. Collected soil samples were enriched for autochthonous bacterial population present therein by adding 10.0 g of collected soil sample in a medium containing 72% soil infusion, 20% nutrient broth, 0.1% lignin, 0.1% vanillin and 0.1% tannin. This suspension was incubated at 37° C. for 48-50 hrs under gentle shaking. The obtained enriched suspension was used for isolating bacterial strains using serial dilution method. Serial dilutions for this purpose were prepared till concentration of $10^{-12}$ in 50 mM phosphate buffer, pH 6.8. Appropriate aliquots of each dilution were plated on different media (listed in Table 1) and plates were incubated at 37° C. for 20-24 hrs in upright position. The number of various bacterial isolates appearing as colonies were noted and further purified for use and storage (see Table 2).

TABLE 1

Various Media Used for Isolating Bacterial Strains from Source Habitat

| Sl. No. | Medium | Medium Composition |
|---|---|---|
| 1. | ASM1 | sludge infusion[a] |
| 2. | SM1 | soil infusion[b] |
| 3. | ASM2 | sludge infusion + 0.1% lignin |
| 4. | SM2 | soil infusion + 0.1% lignin |
| 5. | ASM3 | 50% sludge infusion + 50% Nutrient broth |
| 6. | SM3 | 50% soil infusion + 50% Nutrient broth |
| 7. | M4 | Pulp and paper wastewater |
| 8. | M5 | Nutrient broth + 0.1% lignin |
| 9. | M6 | Nutrient Broth |
| 10. | ASM7 | Sludge infusion - 400 ml; Yeast extract - 3.0 g; Glucose - 7.5 g; $K_2HPO_4$ - 0.5 g; $KH_2PO_4$ - 0.5 g; $MgSO_4$ - 0.5 g; distilled water - 600 ml and lignin - 1.0 |
| 11. | SM7 | Soil infusion - 400 ml; Yeast extract - 3.0 g; Glucose - 7.5 g; $K_2HPO_4$ - 0.5 g; $KH_2PO_4$ - 0.5 g; $MgSO_4$ - 0.5 g; distilled water - 600 ml and lignin - 1.0 |

TABLE 2

Number of Various Bacterial Isolates that Appeared on Different Nutrient Media

| | | Number of bacterial strains isolated | | | | | | | | | | |
|---|---|---|---|---|---|---|---|---|---|---|---|---|
| | | Source: Activated sludge | | | | | | Source: Soil Sample | | | | |
| | Medium | Dilutions at which bacteria are isolated | | | | | | | | | | |
| Sl. No. | No. | $10^{-2}$ | $10^{-4}$ | $10^{-6}$ | $10^{-7}$ | $10^{-8}$ | $10^{-9}$ | $10^{-2}$ | $10^{-4}$ | $10^{-6}$ | $10^{-7}$ | $10^{-8}$ | $10^{-9}$ |
| 1. | ASM1 | 4 | 2 | | | | | | | | | | |
| 2. | SM1 | | | | | | | | 3 | | 1 | 1 | |

TABLE 2-continued

Number of Various Bacterial Isolates that Appeared on Different Nutrient Media

| | | Number of bacterial strains isolated | | | | | | | | | | | |
|---|---|---|---|---|---|---|---|---|---|---|---|---|---|
| | Medium | Source: Activated sludge | | | | | | Source: Soil Sample | | | | | |
| | | Dilutions at which bacteria are isolated | | | | | | | | | | | |
| Sl. No. | No. | $10^{-2}$ | $10^{-4}$ | $10^{-6}$ | $10^{-7}$ | $10^{-8}$ | $10^{-9}$ | $10^{-2}$ | $10^{-4}$ | $10^{-6}$ | $10^{-7}$ | $10^{-8}$ | $10^{-9}$ |
| 3. | ASM2 | | 1 | 3 | 3 | | | | | | | | |
| 4. | SM2 | | | | | | | | 5 | 1 | 3 | 2 | |
| 5. | ASM3 | | | 1 | 1 | 1 | | | | | | | |
| 6. | SM3 | | | | | | | | 2 | 5 | 3 | | |
| 7. | M4 | | | 2 | 2 | 1 | | | 3 | 2 | 4 | | |
| 8. | M5 | | 3 | 3 | 4 | | | | 2 | 3 | 1 | | |
| 9. | M6 | | 1 | 1 | 6 | 4 | | | 4 | 3 | | 1 | |
| 10. | ASM7 | | | 3 | 4 | 1 | | | | | | | |
| 11. | SM7 | | | | | | | 2 | 1 | 1 | 3 | | |

EXAMPLE 2

Activated sludge samples from a selected pulp and paper mill (Century Pulp & Paper Mill, LalKuan, Uttaranchal) were selected for isolation of bacterial strains. Different media were chosen for isolation and are listed in Table 1. The collected samples were enriched for the autochthonous bacterial population present therein, by adding 10.0 ml of the sludge sample in a medium containing 72% soil infusion, 20% nutrient broth, 0.1% lignin, 0.1% vanillin and 0.1% tannin. This suspension was incubated at 37° C. for 48-50 hrs under gentle shaking. The obtained enriched suspension was used for isolating the bacterial strains using the serial dilution method. Serial dilutions for this purpose were prepared from $10^{-1}$ to $10^{-12}$ in 50 mM phosphate buffer, pH 6.8, 100 µl of each dilution were plated on different media (as listed in Table 1) and the plates were incubated at 37° C. for 20-24 hrs in an upright position. The number of various bacterial isolates hat appeared as colonies were noted and further purified for use and storage (see Table 2).

EXAMPLE 3

BOD Analysis of Pulp and Paper Wastewater Sample Using Individual Isolated Bacterial Strains Some of the bacterial strains were chosen randomly from the total isolated strains on the basis of their growth rate for use as seeding material for BOD analysis of pulp and paper wastewater. Those bacterial strains having a comparatively faster growth rate and thus a short generation time were selected for further set of experiments.

| Isolate No. | Measurement of bacterial growth in terms of optical density at 650 nm | | | | |
|---|---|---|---|---|---|
| | 0 hr. | 4 hr. | 8 hr. | 12 hr. | 16 hr. |
| 1. | 0.040 | 0.075 | 0.232 | 1.102 | 1.50 |
| 2. | 0.042 | 0.066 | 0.183 | 1.125 | 1.45 |
| 3. | 0.041 | 0.067 | 0.154 | 1.154 | 1.32 |
| 4. | 0.048 | 0.066 | 0.212 | 1.168 | 1.48 |
| 5. | 0.044 | 0.069 | 0.163 | 0.994 | 1.25 |
| 6. | 0.056 | 0.068 | 0.178 | 0.962 | 1.58 |
| 7. | 0.055 | 0.070 | 0.118 | 0.976 | 1.57 |
| 8. | 0.057 | 0.069 | 0.142 | 0.951 | 1.21 |
| 9. | 0.054 | 0.068 | 0.107 | 0.945 | 1.23 |
| 10. | 0.047 | 0.067 | 0.189 | 0.986 | 1.25 |
| 11. | 0.041 | 0.069 | 0.227 | 1.011 | 1.33 |
| 12. | 0.042 | 0.071 | 0.257 | 1.059 | 1.35 |
| 13. | 0.039 | 0.072 | 0.109 | 1.045 | 1.45 |
| 14. | 0.054 | 0.073 | 0.127 | 1.064 | 1.38 |
| 15. | 0.053 | 0.074 | 0.147 | 0.983 | 1.56 |
| 16. | 0.045 | 0.072 | 0.106 | 1.008 | 1.58 |
| 17. | 0.046 | 0.071 | 0.208 | 0.895 | 1.31 |
| 18. | 0.051 | 0.068 | 0.155 | 0.913 | 1.21 |
| 19. | 0.050 | 0.066 | 0.126 | 0.962 | 1.35 |
| 20. | 0.049 | 0.067 | 0.135 | 0.951 | 1.45 |
| 21. | 0.043 | 0.069 | 0.168 | 0.824 | 1.58 |
| 22. | 0.046 | 0.070 | 0.154 | 0.807 | 1.46 |
| 23. | 0.040 | 0.071 | 0.173 | 0.813 | 1.47 |
| 24. | 0.041 | 0.075 | 0.152 | 0.882 | 1.37 |
| 25. | 0.045 | 0.076 | 0.202 | 0.895 | 1.40 |
| 26. | 0.044 | 0.077 | 0.214 | 0.859 | 1.29 |
| 27. | 0.047 | 0.076 | 0.192 | 0.825 | 1.24 |
| 28. | 0.049 | 0.075 | 0.182 | 0.865 | 1.26 |
| 29. | 0.047 | 0.078 | 0.114 | 0.904 | 1.27 |
| 30. | 0.051 | 0.079 | 0.124 | 0.925 | 1.22 |
| 31. | 0.052 | 0.080 | 0.133 | 0.936 | 1.23 |
| 32. | 0.050 | 0.082 | 0.152 | 0.984 | 1.21 |
| 33. | 0.051 | 0.081 | 0.141 | 0.995 | 1.35 |
| 34. | 0.053 | 0.078 | 0.163 | 0.952 | 1.38 |
| 35. | 0.054 | 0.076 | 0.201 | 0.945 | 1.39 |
| 36. | 0.055 | 0.074 | 0.152 | 1.009 | 1.40 |
| 37. | 0.057 | 0.075 | 0.174 | 1.056 | 1.41 |
| 38. | 0.057 | 0.076 | 0.164 | 1.066 | 1.25 |
| 39. | 0.056 | 0.071 | 0.136 | 1.089 | 1.54 |
| 40. | 0.059 | 0.069 | 0.153 | 1.100 | 157 |
| 41. | 0.058 | 0.068 | 0.104 | 1.114 | 1.59 |
| 42. | 0.057 | 0.067 | 0.131 | 1.010 | 1.51 |
| 43. | 0.056 | 0.066 | 0.147 | 1.028 | 1.49 |
| 44. | 0.058 | 0.069 | 0.154 | 1.158 | 1.45 |
| 45. | 0.060 | 0.070 | 0.162 | 1.163 | 1.43 |
| 46. | 0.061 | 0.071 | 0.171 | 1.190 | 1.53 |
| 47. | 0.059 | 0.073 | 0.236 | 1.177 | 1.32 |
| 48. | 0.062 | 0.0742 | 0.207 | 1.184 | 1.38 |
| 49. | 0.063 | 0.071 | 0.220 | 1.203 | 1.29 |
| 50. | 0.064 | 0.072 | 0.252 | 1.152 | 1.36 |
| 51. | 0.061 | 0.074 | 0.241 | 1.098 | 1.34 |
| 52. | 0.063 | 0.075 | 0.125 | 1.087 | 1.21 |
| 53. | 0.059 | 0.076 | 0.133 | 1.029 | 1.22 |
| 54. | 0.058 | 0.077 | 0.175 | 1.088 | 1.23 |
| 55. | 0.056 | 0.072 | 0.151 | 0.996 | 1.24 |
| 56. | 0.057 | 0.067 | 0.140 | 0.975 | 1.25 |
| 57. | 0.055 | 0.070 | 0.193 | 0.936 | 1.26 |

-continued

| Isolate No. | Measurement of bacterial growth in terms of optical density at 650 nm | | | | |
|---|---|---|---|---|---|
| | 0 hr. | 4 hr. | 8 hr. | 12 hr. | 16 hr. |
| 58. | 0.053 | 0.070 | 0.186 | 0.826 | 1.27 |
| 59. | 0.050 | 0.071 | 0.116 | 0.916 | 1.28 |
| 60. | 0.048 | 0.072 | 0.164 | 1.158 | 1.29 |
| 61. | 0.045 | 0.073 | 0.136 | 0.989 | 1.27 |
| 62. | 0.047 | 0.075 | 0.141 | 0.879 | 1.25 |
| 63. | 0.048 | 0.077 | 0.200 | 0.817 | 1.30 |
| 64. | 0.043 | 0.078 | 0.222 | 0.984 | 1.45 |
| 65. | 0.042 | 0.075 | 0.230 | 0.911 | 1.56 |
| 66. | 0.045 | 0.073 | 0.197 | 0.895 | 1.25 |
| 67. | 0.041 | 0.074 | 0.173 | 0.888 | 1.33 |
| 68. | 0.040 | 0.076 | 0.150 | 0.994 | 1.53 |
| 69. | 0.039 | 0.078 | 0.224 | 0.851 | 1.54 |
| 70. | 0.042 | 0.080 | 0.212 | 0.818 | 1.47 |
| 71. | 0.043 | 0.079 | 0.243 | 0.874 | 1.56 |
| 72. | 0.045 | 0.081 | 0.141 | 0.981 | 1.57 |
| 73. | 0.042 | 0.077 | 0.168 | 1.016 | 1.58 |
| 74. | 0.041 | 0.075 | 0.173 | 1.035 | 1.36 |
| 75. | 0.043 | 0.073 | 0.19 | 1.027 | 1.38 |
| 76. | 0.045 | 0.068 | 0.152 | 1.048 | 1.37 |
| 77. | 0.044 | 0.066 | 0.131 | 1.058 | 1.31 |
| 78. | 0.048 | 0.070 | 0.114 | 1.064 | 1.32 |
| 79. | 0.047 | 0.068 | 0.106 | 1.099 | 1.34 |
| 80. | 0.046 | 0.067 | 0.120 | 1.111 | 1.35 |
| 81. | 0.045 | 0.069 | 0.151 | 1.050 | 1.56 |
| 82. | 0.049 | 0.071 | 0.135 | 1.077 | 1.45 |
| 83. | 0.050 | 0.073 | 0.143 | 1.088 | 1.50 |
| 84. | 0.052 | 0.072 | 0.172 | 1.098 | 1.40 |
| 85. | 0.053 | 0.077 | 0.202 | 1.100 | 1.59 |
| 86. | 0.054 | 0.075 | 0.212 | 1.119 | 1.58 |
| 87. | 0.051 | 0.074 | 0.233 | 1.126 | 1.57 |
| 88. | 0.049 | 0.078 | 0.162 | 0.838 | 1.54 |
| 89. | 0.053 | 0.079 | 0.182 | 0.869 | 1.30 |
| 90. | 0.054 | 0.075 | 0.145 | 0.876 | 1.36 |
| 91. | 0.055 | 0.068 | 0.171 | 0.899 | 1.51 |
| 92. | 0.057 | 0.066 | 0.224 | 0.950 | 1.57 |
| 93. | 0.058 | 0.067 | 0.203 | 0.965 | 1.49 |
| 94. | 0.059 | 0.070 | 0.194 | 0.977 | 1.42 |
| 95. | 0.060 | 0.073 | 0.133 | 1.153 | 1.53 |
| 96. | 0.061 | 0.074 | 0.158 | 1.146 | 1.55 |
| 97. | 0.062 | 0.076 | 0.214 | 1.176 | 1.56 |
| 98. | 0.063 | 0.082 | 0.253 | 1.184 | 1.57 |
| 99. | 0.064 | 0.081 | 0.231 | 1.120 | 1.58 |
| 0 | 0.045 | 0.060 | 0.141 | 1.190 | 1.30 |

EXAMPLE 4

The bacterial strains selected as stated above were individually inoculated in 50 ml of nutrient broth having 0.01% Tween-80, All the cultures were incubated at 37° C. for 16-20 hrs in an incubator shaker at 120 rpm. Optical density of all the cultures was maintained to 1.0±0.1 (at 620 nm). Cells were harvested by centrifugation at 5000 rpm for 15-20 min at a temperature ranging between 4° C. The pellet thus obtained was washed twice with 50 mM phosphate buffer, pH 6.8 by suspending it in 5.0-10.0 ml of the same buffer, vortexing for 30-45 sec followed by centrifugation at 5000 rpm for 20 min at 4° C. The cell pellet of individual bacterial isolates thus obtained was resuspended in 5.0 ml of the same buffer and used as seeding material @ 0.1% and 0.2% for the BOD analysis of pulp and paper wastewater using GGA as a reference standard. The results of the study are presented in Table 3.

TABLE 3

BOD analysis of pulp and paper wastewater sample using individual isolated bacterial strains

| | | BOD (mg/l) | | | |
|---|---|---|---|---|---|
| | | GGA: 300 mg/l BOD: 204 mg/l by BODSEED | | Pulp and paper wastewater (COD: 240 mg/l) BOD: 80 mg/l by BODSEED ™ | |
| Sl. No. | Bacterial Isolates | 0.1% seed | 0.2% seed | 0.1% seed | 0.2% seed |
| 1. | Isolate 1 | 175 | 177 | 130 | 132 |
| 2. | Isolate 2 | 169 | 165 | 118 | 116 |
| 3. | Isolate 4 | 179 | 152 | 121 | 121 |
| 4. | Isolate 6 | 182 | 182 | 130 | 108 |
| 5. | Isolate 7 | 160 | 165 | 101 | 112 |
| 6. | Isolate 13 | 184 | 179 | 124 | 126 |
| 7. | Isolate 14 | 171 | 178 | 136 | 130 |
| 8. | Isolate 15 | 178 | 171 | 126 | 120 |
| 9. | Isolate 16 | 166 | 173 | 110 | 118 |
| 10. | Isolate 20 | 204 | 200 | 108 | 112 |
| 11. | Isolate 21 | 157 | 151 | 100 | 108 |
| 12. | Isolate 22 | 87 | 80 | 05 | 10 |
| 13. | Isolate 23 | 90 | 92 | 08 | 24 |
| 14. | Isolate 24 | 95 | 107 | 07 | 21 |
| 15. | Isolate 25 | 110 | 101 | 11 | 30 |
| 16. | Isolate 35 | 108 | 121 | 24 | 41 |
| 17. | Isolate 36 | 125 | 120 | 32 | 52 |
| 18. | Isolate 37 | 112 | 118 | 60 | 64 |
| 19. | Isolate 39 | 186 | 180 | 85 | 87 |
| 20. | Isolate 40 | 181 | 179 | 88 | 80 |
| 21. | Isolate 41 | 185 | 188 | 90 | 95 |
| 22. | Isolate 42 | 192 | 190 | 95 | 97 |
| 23. | Isolate 43 | 190 | 185 | 109 | 101 |
| 24. | Isolate 44 | 70 | 76 | 41 | 43 |
| 25. | Isolate 45 | 195 | 197 | 117 | 120 |
| 26. | Isolate 46 | 190 | 184 | 116 | 120 |
| 27. | Isolate 64 | 171 | 168 | 125 | 115 |
| 28. | Isolate 65 | 78 | 60 | 20 | 30 |
| 29. | Isolate 68 | 75 | 80 | 28 | 32 |
| 30. | Isolate 69 | 168 | 173 | 121 | 128 |
| 31. | Isolate 70 | 171 | 178 | 124 | 121 |
| 32. | Isolate 71 | 180 | 168 | 113 | 121 |
| 33. | Isolate 72 | 171 | 172 | 99 | 108 |
| 34. | Isolate 73 | 177 | 170 | 98 | 108 |
| 35. | Isolate 81 | 140 | 135 | 21 | 28 |
| 36. | Isolate 82 | 175 | 171 | 112 | 113 |
| 37. | Isolate 83 | 168 | 170 | 108 | 109 |
| 38. | Isolate 84 | 131 | 121 | 31 | 39 |
| 39. | Isolate 85 | 127 | 120 | 55 | 50 |
| 40. | Isolate 86 | 105 | 113 | 51 | 59 |
| 41. | Isolate 87 | 101 | 91 | 60 | 68 |
| 42. | Isolate 88 | 170 | 172 | 121 | 124 |
| 43. | Isolate 91 | 173 | 177 | 117 | 117 |
| 44. | Isolate 92 | 168 | 168 | 110 | 108 |
| 45. | Isolate 93 | 92 | 100 | 34 | 36 |
| 46. | Isolate 94 | 97 | 105 | 51 | 55 |
| 47. | Isolate 95 | 68 | 70 | 62 | 38 |
| 48. | Isolate 96 | 71 | 78 | 36 | 46 |
| 49. | Isolate 97 | 82 | 90 | 41 | 34 |
| 50. | Isolate 98 | 87 | 81 | 48 | 50 |
| 51. | Isolate 99 | 101 | 107 | 52 | 52 |

EXAMPLE 5

BOD Analysis of Pulp and Paper Wastewater Using Different Formulated Microbial Consortium Out of the total individual bacterial isolates used for BOD analysis, as described in Example 3, 27 isolates were selected for the formulation of 44 microbial consortia (Table 4) Those individual bacterial isolates, which exhibited BOD values higher to or comparable to BODSEED™ were chosen.

TABLE 4

Microbial consortia as made from selected bacterial isolates

| Sl. No. | Microbial consortium | Selected Isolates |
|---|---|---|
| 1. | Consortium 1 (Seed) | Isolate 2, Isolate 69 and Isolate 88 |
| 2. | Consortium 2 (Seed) | Isolate 20, Isolate 43 and Isolate 64 |
| 3. | Consortium 3 (Seed) | Isolate 71, Isolate 88 and Isolate 92 |
| 4. | Consortium 4 (Seed) | Isolate 1, Isolate 64 and Isolate 71 |
| 5. | Consortium 5 (Seed) | Isolate 7, Isolate 21 and Isolate 43 |
| 6. | Consortium 6 (Seed) | Isolate 6, Isolate 20 and Isolate 66 |
| 7. | Consortium 7 (Seed) | Isolate 15, Isolate 21 and Isolate 92 |
| 8. | Consortium 8 (Seed) | Isolate 46, Isolate 71 and Isolate 16 |
| 9. | Consortium 9 (Seed) | Isolate 13, Isolate 43 and Isolate 43 |
| 10. | Consortium 10 (Seed) | Isolate 4, Isolate 15 and Isolate 91 |
| 11. | Consortium 11 (Seed) | Isolate 21, Isolate 73 and Isolate 88 |
| 12. | Consortium 12 (Seed) | Isolate 13, Isolate 15 and Isolate 91 |
| 13. | Consortium 13 (Seed) | Isolate 45, Isolate 46 and Isolate 88 |
| 14. | Consortium 14 (Seed) | Isolate 43, Isolate 73 and Isolate 83 |
| 15. | Consortium 15 (Seed) | Isolate 6, Isolate 88 and Isolate 92 |
| 16. | Consortium 16 (Seed) | Isolate 72, Isolate 91 and Isolate 92 |
| 17. | Consortium 17 (Seed) | Isolate 16, Isolate 45 and Isolate 88 |
| 18. | Consortium 18 (Seed) | Isolate 6, Isolate 46 and Isolate 82 |
| 19. | Consortium 19 (Seed) | Isolate 72, Isolate 92 and Isolate 91 |
| 20. | Consortium 20 (Seed) | Isolate 21, Isolate 46 and Isolate 88 |
| 21. | Consortium 21 (Seed) | Isolate 20, Isolate 83 and Isolate 91 |
| 22. | Consortium 22 (Seed) | Isolate 6, Isolate 64 and Isolate 70 |
| 23. | Consortium 23 (Seed) | Isolate 64, Isolate 73 and Isolate 83 |
| 24. | Consortium 24 (Seed) | Isolate 20, Isolate 88 and Isolate 92 |
| 25. | Consortium 25 (Seed) | Isolate 13, Isolate 45 and Isolate 73 |
| 26. | Consortium 26 (Seed) | Isolate 82, Isolate 92 and Isolate 88 |
| 27. | Consortium 27 (Seed) | Isolate 2, Isolate 71 and Isolate 92 |
| 28. | Consortium 28 (Seed) | Isolate 21, Isolate 69 and Isolate 71 |
| 29. | Consortium 29 (Seed) | Isolate 14, Isolate 15 and Isolate 45 |
| 30. | Consortium 30 (Seed) | Isolate 1, Isolate 73 and Isolate 83 |
| 31. | Consortium 31 (Seed) | Isolate 43, Isolate 71 and Isolate 92 |
| 32. | Consortium 32 (Seed) | Isolate 21, Isolate 43 and Isolate 45 |
| 33. | Consortium 33 (Seed) | Isolate 21, Isolate 82and Isolate 99 |
| 34. | Consortium 34 (Seed) | Isolate 20, Isolate 70 and Isolate 46 |
| 35. | Consortium 35 (Seed) | Isolate 64, Isolate 88 and Isolate 92 |
| 36. | Consortium 36 (Seed) | Isolate 2, Isolate 70 and Isolate 92 |
| 37. | Consortium 37 (Seed) | Isolate 20, Isolate 91 and Isolate 92 |
| 38. | Consortium 38 (Seed) | Isolate 46, Isolate 69 and Isolate 83 |
| 39. | Consortium 39 (Seed) | Isolate 14, Isolate 64 and Isolate 73 |
| 40. | Consortium 40 (Seed) | Isolate 46, Isolate 92 and Isolate 88 |
| 41. | Consortium 41 (Seed) | Isolate 2, Isolate 45 and Isolate 82 |
| 42. | Consortium 42 (Seed) | Isolate 43, Isolate 83 and Isolate 91 |
| 43. | Consortium 43 (Seed) | Isolate 4, Isolate 45 and Isolate 82 |
| 44. | Consortium 44 (Seed) | Isolate 73, Isolate 88 and Isolate 92 |

EXAMPLE 6

The individual bacterial strains comprising the said microbial consortium were inoculated separately in 50 ml of nutrient broth having 0.01% Tween-80. All the cultures were incubated at 37° C. for 16-20 hrs in an incubator shaker at 120 rpm. Optical density of all the cultures was maintained to 1.0±0.1 (at 620 nm). The individual cell suspensions were mixed in desired proportions to obtain different microbial consortia. Cells of each microbial consortium were harvested by centrifugation at 5000-7000 rpm for 15-20 min at a temperature rid between 4-10° C. The pellet thus obtained was washed twice with 50 mM phosphate buffer, pH 6.8 by suspending it in 5.0-10.0 ml of the same buffer, vortexing for 30-45 sec followed by centrifugation at 5000-7000 rpm for 20 min at 4° C. The cell pellet thus obtained was resuspended in 5.0 ml of the same buffer and used as seeding material @ 0.1% for the BOD analysis of pulp and paper wastewater using GGA as a reference standard. The results of the BOD analysis performed using the microbial seeds obtained in the above said manner are illustrated in Table 5.

TABLE 5

BOD analysis of pulp and paper wastewater using different formulated microbial consortia

| | | BOD (mg/l) | |
|---|---|---|---|
| Sl. No. | Microbial consortium | GGA: 300 mg/l | Pulp and paper wastewater (COD: 410 mg/l) BOD: 130 mg/l by BODSEED |
| 1. | Consortium 1 (Seed) | 119 | 77 |
| 2. | Consortium 2 (Seed) | 189 | 92 |
| 3. | Consortium 3 (Seed) | 118 | 76 |
| 4. | Consortium 4 (Seed) | 147 | 54 |
| 5. | Consortium 5 (Seed) | 182 | 79 |
| 6. | Consortium 6 (Seed) | 146 | 99 |
| 7. | Consortium 7 (Seed) | 179 | 99 |
| 8. | Consortium 8 (Seed) | 150 | 72 |
| 9. | Consortium 9 (Seed) | 150 | 93 |
| 10. | Consortium 10 (Seed) | 84 | 45 |
| 11. | Consortium 11 (Seed) | 124 | 57 |
| 12. | Consortium 12 (Seed) | 118 | 66 |
| 13. | Consortium 13 (Seed) | 128 | 60 |
| 14. | Consortium 14 (Seed) | 128 | 52 |
| 15. | Consortium 15 (Seed) | 97 | 60 |
| 16. | Consortium 16 (Seed) | 05 | 03 |
| 17. | Consortium 17 (Seed) | 131 | 117 |
| 18. | Consortium 18 (Seed) | 165 | 145 |
| 19. | Consortium 19 (Seed) | 139 | 103 |
| 20. | Consortium 20 (Seed) | 131 | 91 |
| 21. | Consortium 21 (Seed) | 140 | 101 |
| 22. | Consortium 22 (Seed) | 154 | 78 |
| 23. | Consortium 23 (Seed) | 172 | 157 |
| 24. | Consortium 24 (Seed) | 156 | 135 |
| 25. | Consortium 25 (Seed) | 140 | 193 |
| 26. | Consortium 26 (Seed) | 147 | 157 |
| 27. | Consortium 27 (Seed) | 153 | 137 |
| 28. | Consortium 28 (Seed) | 136 | 131 |
| 29. | Consortium 29 (Seed) | 154 | 100 |
| 30. | Consortium 30 (Seed) | 160 | 82 |
| 31. | Consortium 31 (Seed) | 153 | 107 |
| 32. | Consortium 32 (Seed) | 158 | 123 |
| 33. | Consortium 33 (Seed) | 144 | 90 |
| 34. | Consortium 34 (Seed) | 164 | 73 |
| 35. | Consortium 35 (Seed) | 111 | 112 |
| 36. | Consortium 36 (Seed) | 120 | 145 |
| 37. | Consortium 37 (Seed) | 144 | 128 |
| 38. | Consortium 38 (Seed) | 150 | 154 |
| 39. | Consortium 39 (Seed) | 168 | 178 |
| 40. | Consortium 40 (Seed) | 168 | 135 |
| 41. | Consortium 41 (Seed) | 170 | 172 |
| 42. | Consortium 42 (Seed) | 154 | 124 |
| 43. | Consortium 43 (Seed) | 143 | 120 |
| 44. | Consortium 44 (Seed) | 158 | 140 |

EXAMPLE 7

Some of the microbial consortia used for the BOD analysis (described in Example 6) were selected for further set of experiments on the basis of their ability to biodegrade the constituents of pulp and paper wastewater, thereby exerting an oxygen demand comparable to or higher than that exerted by BODSEED™. The selected microbial consortia were again tested for the BOD analysis of a fresh lot of pulp and paper wastewater. The resulting BOD values are presented in Table 6.

TABLE 6

BOD analysis of pulp and paper wastewater using selected microbial consortia

| | | BOD (mg/l) | |
|---|---|---|---|
| Sl. No. | Microbial consortium | GGA: 300 mg/l | Pulp and paper wastewater (COD: 328 mg/l) BOD: 109 mg/l by BODSEED |
| 1. | Consortium 2 (Seed) | 176 | 66 |
| 2. | Consortium 6 (Seed) | 168 | 101 |
| 3. | Consortium 7 (Seed) | 176 | 97 |
| 4. | Consortium 9 (Seed) | 194 | 94 |
| 5. | Consortium 17 (Seed) | 142 | 119 |
| 6. | Consortium 18 (Seed) | 148 | 156 |
| 7. | Consortium 23 (Seed) | 141 | 153 |
| 8. | Consortium 24 (Seed) | 127 | 142 |
| 9. | Consortium 25 (Seed) | 123 | 152 |
| 10. | Consortium 26 (Seed) | 126 | 147 |
| 11. | Consortium 27 (Seed) | 128 | 156 |
| 12. | Consortium 28 (Seed) | 141 | 150 |
| 13. | Consortium 32 (Seed) | 154 | 152 |
| 14. | Consortium 35 (Seed) | 146 | 143 |
| 15. | Consortium 36 (Seed) | 151 | 154 |
| 16. | Consortium 38 (Seed) | 158 | 159 |
| 17. | Consortium 39 (Seed) | 161 | 164 |
| 18. | Consortium 41 (Seed) | 160 | 162 |

EXAMPLE 8

Out of the 14 microbial consortia selected for BOD analysis (described in Example 7), 5 microbial consortia were selected, which exhibited the best values for pulp and paper wastewater. The results were repeated with three samples, collected at different time intervals for authentication (see Table 7).

TABLE 7

BOD analysis of pulp and paper wastewater using best performing microbial consortia

| | | BOD (mg/l)* | |
|---|---|---|---|
| Sl. No. | Microbial consortium | GGA: 300 mg/l | Pulp and paper wastewater (COD: 312 mg/l) BOD: 94 mg/l by BODSEED |
| 1. | Consortium 23 (Seed) | 144 | 150 |
| 2. | Consortium 25 (Seed) | 134 | 154 |
| 3. | Consortium 38 (Seed) | 159 | 159 |
| 4. | Consortium 39 (Seed) | 160 | 162 |
| 5. | Consortium 41 (Seed) | 168 | 165 |

*all values are mean of the analysis done with three different samples

EXAMPLE 9

Out of the best five microbial consortia, the following consortium was selected as an authenticated and best seeding material for the estimation of accurate and reproducible estimation of biochemical oxygen demand of pulp and paper industrial wastewater. The bacterial strains in this consortium were identified as *Micrococcus* sp. (MTCC 6602), *Staphylococcus* sp. (MTCC 6603), *Kurthia zopfii* (MTCC 6604), *Alcaligenes faecalis* (MTCC 6719) and *Pseudomonas aerations* (MTCC 6605) which are deposited at International Depository at IMTECH, Sector 39A, Chandigarh, India

TABLE 8

BOD analysis of pulp and paper wastewater using best performing microbial consortia

| | | BOD (mg/l)* | |
|---|---|---|---|
| Sl. No. | Microbial consortium | GGA: 300 mg/l | Pulp and paper wastewater (COD: 312 mg/l) BOD: 94 mg/l by BODSEED |
| 1. | Consortium 41 (Seed) | 168 | 165 |

*all values are mean of the analysis done with three different samples

Advantages

1. The selected formulated microbial consortium comprising of the isolated bacterial strains act in a synergistic way and is capable of degrading the easily assailable as well as the refractory organic compounds present in Pulp and paper wastewater.
2. These types of seeds will detail the quantity of organic compounds contained in these wastes, which is released unnoticed when the wastes are analyzed for their BOD load using the general seeds. This leads to accurate BOD values of these types of wastewaters, which is difficult to achieve with the microorganisms present in general seeding material.
3. The use of such specific seeding material for the BOD analysis of Pulp and paper wastewaters will lead to a better control of the treatment process of these types of wastewaters.

We claim:

1. An isolated composition for estimation of accurate and reproducible biochemical oxygen demand of pulp and paper industrial waste water, the isolated composition comprising five bacterial strains, *Micrococcus* sp. (MTCC 5198), *Staphylococcus* sp. (MTCC 5199), *Kurthia zopfii* (MTCC 5200), *Alcaligenes faecalis* (MTCC 5201) and *Pseudomonas aeruginosa* (MTCC 5202) which are deposited at International Depository at IMTECH, Sector 39A, Chandigarh, India.

2. The isolated composition as claimed in claim 1 wherein the five bacterial strains are present in equal proportion.

3. The isolated composition as claimed in claim 1, wherein the bacteria are isolated from activated sludge and soil samples collected from the vicinity of a selected pulp and paper mill located in India.

4. An isolated composition for estimation of accurate and reproducible biochemical oxygen demand of pulp and paper industrial waste water, comprising *Micrococcus* sp. (MTCC 5198), *Staphylococcus* sp. (MTCC 5199), *Kurthia zopfii* (MTCC 5200), *Alcaligenes faecalis* (MTCC 5201) and *Pseudomonas aeruginosa* (MTCC 5202), which are deposited at International Depository at IMTECH, Sector 39A, Chandigarh, India, wherein the characteristics of *Micrococcus* sp. (MTCC 5198) are as follows: Gram-positive, cocci shaped, aerobic, motile, capable to grow at NaCl (8.5%) and capable to hydrolyze urea and starch, wherein the characteristics of *Staphylococcus* sp. (MTCC 5199) are as follows: Gram-positive, rod shaped, aerobic, non-motile, capable to grow up to pH 11.00 and capable to utilize cellobiose and salicin, wherein the characteristics of *Kurthia zopfii* (MTCC 5200) are as follows: Gram-negative, rod shaped, facultative aerobic, motile, capable to grow at high pH (11.00) and capable to utilize cellobiose and raffinose, wherein the characteristics of *Alcaligenes faecalis* (MTCC 5201) are as follows: Gram-negative, rod shaped, aerobic, motile, positive for cytochrome oxidase and catalase test and capable to utilize dextrose and galatose as carbon source, and wherein the characteristics of *Pseudomonas aeruginosa* (MTCC 5202) are as follows: Gram-negative, rod shaped, aerobic motile, fluorescent and capable to utilize arabinose, dextrose, fructose, galactose, mannitol, mannose and xylose.

* * * * *